US010252029B2

(12) United States Patent
Hou et al.

(10) Patent No.: US 10,252,029 B2
(45) Date of Patent: Apr. 9, 2019

(54) CATHETER OR GUIDE WIRE MANIPULATING DEVICE WITH TWO-POINT-CLAMPING FOR VASCULAR INTERVENTION

(71) Applicant: INSTITUTE OF AUTOMATION, CHINESE ACADEMY OF SCIENCES, Haidan District, Beijing (CN)

(72) Inventors: Zengguang Hou, Beijing (CN); Guibin Bian, Beijing (CN); Xiaoliang Xie, Beijing (CN); Long Cheng, Beijing (CN); Min Tan, Beijing (CN); Zhenqiu Feng, Beijing (CN); Xiaohu Zhou, Beijing (CN)

(73) Assignee: INSTITUTE OF AUTOMATION, CHINESE ACADEMY OF SCIENCES, Haidian District, Beijing (CN)

( * ) Notice: Subject to any disclaimer, the term of this patent is extended or adjusted under 35 U.S.C. 154(b) by 784 days.

(21) Appl. No.: 14/770,232

(22) PCT Filed: Jun. 25, 2013

(86) PCT No.: PCT/CN2013/077884
§ 371 (c)(1),
(2) Date: Nov. 12, 2015

(87) PCT Pub. No.: WO2014/127599
PCT Pub. Date: Aug. 28, 2014

(65) Prior Publication Data

US 2016/0184552 A1 Jun. 30, 2016

(30) Foreign Application Priority Data

Feb. 25, 2013 (CN) .......................... 2013 1 0058140

(51) Int. Cl.
*A61M 31/00* (2006.01)
*A61M 37/00* (2006.01)
(Continued)

(52) U.S. Cl.
CPC .. *A61M 25/0113* (2013.01); *A61M 25/09041* (2013.01); *A61B 2034/301* (2016.02)

(58) Field of Classification Search
CPC ................ A61B 34/20; A61B 19/2203; A61B 2019/2211; A61M 25/0105; A61M 25/0113; A61M 25/09041
(Continued)

(56) References Cited

U.S. PATENT DOCUMENTS 7,998,020 B2 8/2011 Kidd et al.
2004/0254566 A1* 12/2004 Plicchi .................. A61B 34/70 606/1
(Continued)

FOREIGN PATENT DOCUMENTS

CN 101933837 A 1/2011
CN 103083783 A 5/2013
(Continued)

OTHER PUBLICATIONS

International Search Report for corresponding International Patent Application No. PCT/CN2013/077884 dated Nov. 28, 2013.

*Primary Examiner* — Jason Flick
(74) *Attorney, Agent, or Firm* — Merchant & Gould P.C.

(57) ABSTRACT

A catheter or guide wire manipulating device with two-point-clamping for vascular intervention is provided, comprising a thumb component (3), a forefinger component (4), a driving component (1) and a catheter/guide wire support component (2); the thumb component (3) comprises a pair of rollers (9, 10) configured to advance or retreat the catheter/guide wire; the thumb component (3) is configured to drive
(Continued)

the catheter/guide wire to rotate clockwise or counterclockwise through a combination motion of the components; the forefinger component (4) is configured to implement the rotation and the advancement of the catheter/guide wire by moving manually away from the thumb component (3), and returning by a pull force of a spring (27) after being released; the driving component (2) is configured to drive the thumb component (3) and the forefinger component (4); the catheter/guide wire support component comprises a Y adapter fixation configured to install a Y adapter and an entry support configured to support and guide the catheter/guide wire into a mechanism.

6 Claims, 5 Drawing Sheets

(51) Int. Cl.

| | |
|---|---|
| ***A61M 25/01*** | (2006.01) |
| ***A61M 25/09*** | (2006.01) |
| *A61B 34/30* | (2016.01) |

(58) Field of Classification Search
USPC .................................................... 604/95.01
See application file for complete search history.

(56) References Cited

U.S. PATENT DOCUMENTS

2009/0105645 A1* 4/2009 Kidd .................. A61M 25/0113 604/108
2011/0264038 A1* 10/2011 Fujimoto ......... A61B 17/12022 604/95.01

FOREIGN PATENT DOCUMENTS

| | | |
|---|---|---|
| CN | 103083784 A | 5/2013 |
| CN | 103157170 A | 6/2013 |
| EP | 1 442 720 A1 | 8/2004 |

* cited by examiner

CATHETER OR GUIDE WIRE MANIPULATING DEVICE WITH TWO-POINT-CLAMPING FOR VASCULAR INTERVENTION

This application is a National Stage Application of PCT/CN2013/077884, filed 25 Jun. 2013, which claims benefit of Serial No. 201310058140.X, filed 25 Feb. 2013 in China and which applications are incorporated herein by reference. A claim of priority is made to each of the above disclosed applications.

TECHNICAL FIELD

The disclosure generally relates to a technical field of medical equipments, and more particularly, to a catheter or guide wire manipulating device with two-point-clamping for vascular intervention.

BACKGROUND

Vascular intervention may be implemented by, under a guidence of a digital subtraction angiography (DSA) system, manipulating a catheter inside human vessels with a surgeon and treating deseases to realize angiostegnosis dialation and angioplasty.

Conventionally, the vascular intervention is mainly done manually by the surgeons. Main disadvantages include 1) long time operation under the X-ray imaging will cause severe damage to the surgeons' health; 2) the conventional operation method requires high manipulation skills, long training time, and has high risk; and 3) factors, such as complicated operations, long operation time and fatigue of surgeons and unstable operation factors, will directly affect a quality of operation and latter patients' recovery. These shortcomings limit a further application of the vascular intervention. Therefore, it is needed a solution to adopt a robotic technology to the vacular intervention.

To solve above problems, Hansen Meidical improved a structure of catheter and then developed an active catheter system. However, a size of the developed catheter is too bigger and this narrows its application. Beihang University made an advancing catheter mechanism, but its assembly, disassembly and sterilization are inconvenient. Institute of Automation, Chinese Academy of Sciences designed an advancing catheter mechanism to imitate human's manipulation, but it cannot allow the catheter to advance continuously. In addition, it is unable to allow simultaneous advancement and rotation of a catheter/guide wire.

SUMMARY

In view of the foregoing, the present disclosure provides a catheter or guide wire manipulating device with two-point-clamping capable of driving the catheter/guide wire to implement an advancement motion, a rotation motion or a simultaneous combination of the both inside vessels.

A catheter or guide wire manipulating device with two-point-clamping for vascular intervention is provided, comprising a thumb component, a forefinger component, a driving component and a catheter/guide wire support component; the thumb component comprises a set of rollers configured to advance or retreat the catheter/guide wire; the thumb component is configured to drive the catheter/guide wire to rotate clockwise or counterclockwise through a combination motion of the thumb component and the forefinger component; the forefinger component is configured to cooperate with the thumb component to implement the rotation and advancement of the catheter/guide wire by moving the forefinger component manually away from the thumb component, and returning by a pull force of a spring after being released; the driving component is configured to drive the thumb component and the forefinger component; the catheter/guide wire support component comprises a Y adapter fixation configured to install a Y adapter and an entry support configured to support and guide the catheter/guide wire into the device.

When the catheter/guide wire is manipulated by the manipulating device to advance and retreat, a two-point contact is formed between two pairs of rollers and the catheter/guide wire. Compared to a single-point contact, a contact area and an upper limit of friction for driving the catheter/guide wire may be increased. In addition, relative to a line contact formed by a pair of belts, the two-point contact can reduce loss of control accuracy caused by errors in shape and position of manipulating device. Therefore, maneuverability of the catheter/guide wire can be improved effectively.

DETAILED DESCRIPTION OF EMBODIMENTS

Figure 1:
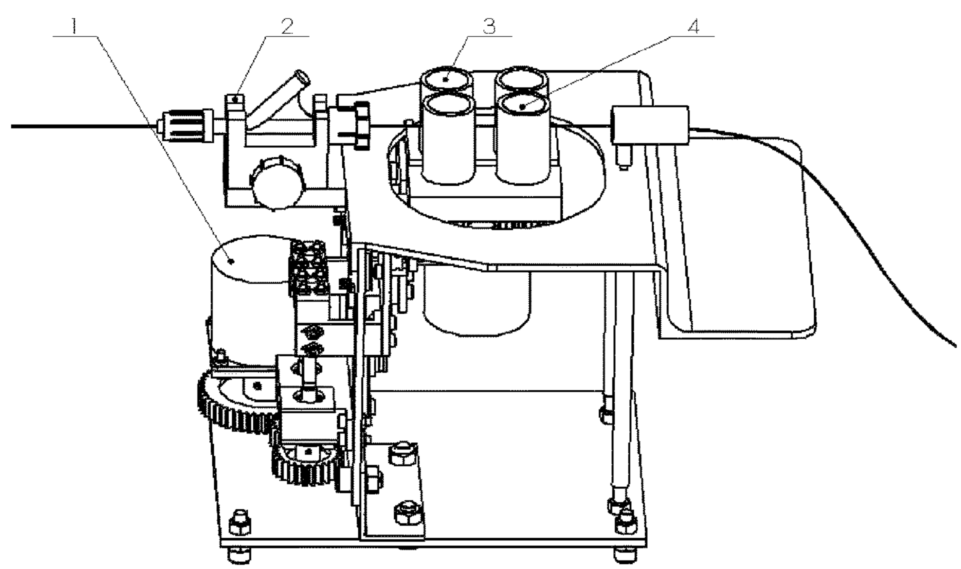
FIG. 1 shows an overall structure of the catheter or guide wire manipulating device with two-point-clamping for vascular intervention according to an embodiment of the disclosure.

For the object, technical solutions and advantages of the disclosure to be more clear and apparent, the disclosure will further elucidated in conjunction with detailed embodiments and with reference to accompanying drawings in the following.

Reference Signs:

driving component 1, catheter/guide wire support component 2, thumb component 3, forefinger component 4, connecting plate 5, guide rail 6, bearing unit 7, rubber cover 8, roller 9, roller 10, rubber cover 11, gear 12, gear 13, gear 14, motor frame 15, advancing motor 16, connecting plate 17, forefinger component base board 18, horizontal guide rail 19, vertical guide rail 20, bearing unit 21, roller shaft 22, rubber cover 23, roller shaft 24, rubber cover 25, limit block 26, spring 27 nut connecting frame 28, nut connecting frame 29, screw rod 30, screw rod 31, bearing unit 32, base board 33, pinion 34, pinion 35, gear 36, motor frame 37, rotating motor 38, Y adapter frame unit 39, top plate 40, support rack 41.

FIG. 1 shows a structure of the catheter or guide wire manipulating device with two-point-clamping for vascular intervention according to an embodiment of the disclosure.

As shown in FIG. 1, the manipulating device may include a thumb component 3, a forefinger component 4, a driving component 1, and a catheter/guide wire support component 2 and drive the catheter/guide wire to advance, rotate or advance while rotate inside the human vessels. The thumb component 3 includes a set of rollers to make the catheter/guide wire advance or retreat. The thumb component 3 and the forefinger component 4 can drive the catheter/guide wire to rotate clockwise and counterclockwise through a combination motion of two fingers. The forefinger component 4 cooperates with the thumb component 3 to realize the rotation and the advancement of the catheter/guide wire. The forefinger component 4 can be moved manually away from the thumb component 3. After being released, the forefinger component 4 returns due to the pull force of the spring. The driving component 1 is configured to move the thumb component 3 and the forefinger component 4. The catheter/guide wire support component 2 includes a Y adapter fixation and an entry support. The Y adapter fixation is used to install a Y adapter quickly, and the entry support can support and guide the catheter/guide wire effectively into the mechanism. The catheter or guide wire manipulating device drives the catheter/guide wire to move along two directions: advancement and rotation. An advancement mechanism of the catheter/guide wire is attached to the rotation mechanism. When clamping the catheter/guide wire, the forefinger component 4 can be moved manually away from the thumb component 3. After being released, the forefinger component 4 returns by the pull force of the spring. The spring of forefinger component 4 makes two pairs of rollers respectively and tightly press the catheter/guide wire. Then a two-point contact is formed between the manipulating device and the catheter/guide wire so as to increase the contact area and the upper limit of friction between rubber covers and the catheter/guide wire. In addition, a certain amount of errors in the shape and the position can be allowed for two pairs of rollers and the maneuverability of the catheter/guide wire is improved.

Figure 2:
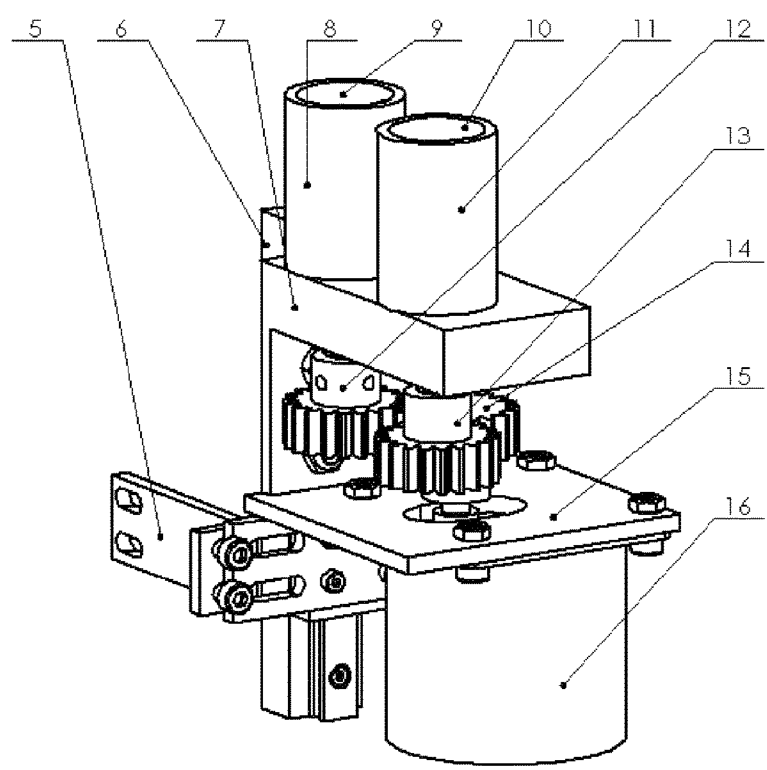
FIG. 2 shows a structure of the thumb component of the catheter or guide wire manipulating device with two-point-clamping for vascular intervention according to the embodiment of the disclosure.

FIG. 2 shows a structure of thumb component 3. Referring to FIG. 2, the thumb component 3 may include a roller 9, a rubber cover 8, a roller 10, a rubber cover 11, a bearing unit 7, a gear 12, a gear 13, a gear 14, a motor frame 15, an advancing motor 16, a guide rail 6, and a connecting plate 5. The advancing motor 16 and a motor frame 15 are fixed together with bolts. The output shaft of the advancing motor 16 transmits the movement to the roller 9 through the engagement between the gear 14 and the gear 12. Then the movement is transmitted to the roller 10 through the engagement between the gear 14 and the gear 13. Roller 9 and 10 rotate with the same angular velocity since two pairs of transmission ratio are the same. The Rollers 9 and 10 are supported fixedly by the bearing unit 7. The Rubber covers 8 and 11 are mounted on roller 9 and 10 respectively by an interference fit.

The Rubber covers 8 and 11 of the thumb component 3 make the catheter/guide wire advance or retreat by rotating clockwise or counterclockwise simultaneously. The transmission is as follows. The output shaft of the advancing motor 16 rotates to make the rollers 9 and 10 moveby a gear transmission, and drives the catheter/guide wire to advance or retreat by a pressure between the rubber covers 8, 11 and the two rubber covers of the forefinger component 4.

The thumb component 3 and the forefinger component 4 can drive the catheter/guide wire to rotate in a clockwise or a counterclockwise direction through a combination motion of two fingers by connecting the rollers 9 and 10, the rubber covers 8 and 11, the bearing unit 7, the motor frame 15, the gears 12, 13 and 14, and the advancing motor 16 of the thumb component as a whole part to the driving component 1 through the connecting plate 5, moving the whole part linearly up and down with the guidance of guide rail 6 while driving the rollers of the forefinger component 4 by the driving component 1 to move linearly in an opposite direction to a motion direction of the whole part.

Figure 3:
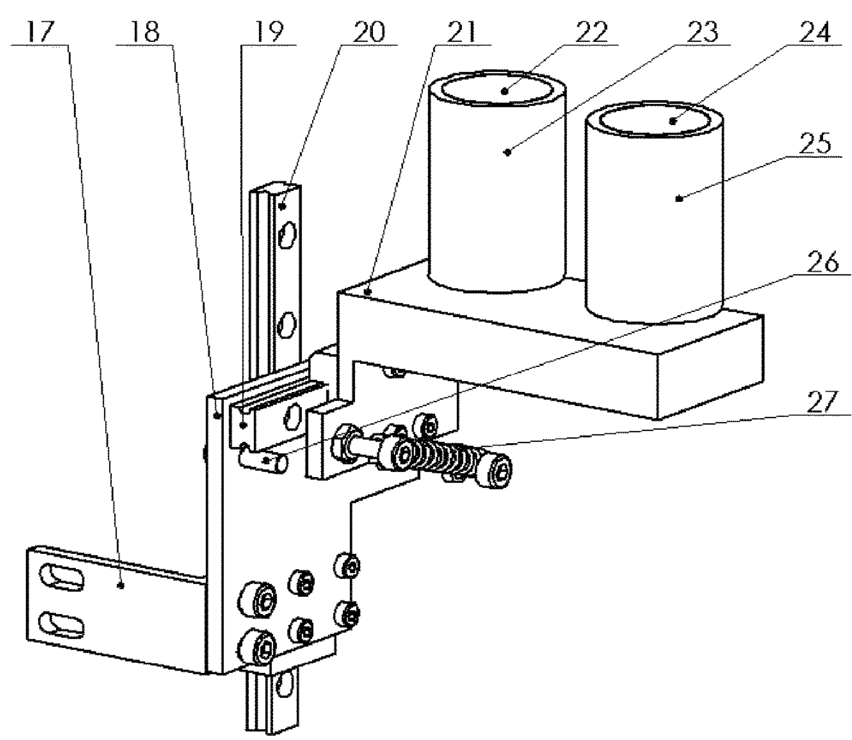
FIG. 3 shows a structure of the forefinger component of the catheter or guide wire manipulating device with two-point-clamping for vascular intervention according to the embodiment of the disclosure.

FIG. 3 shows a structure of forefinger component 4. Referring to FIG. 3, the forefinger component 4 may include rollers 22, 24, rubber covers 23, 25, a bearing unit 21, a horizontal guide rail 19, a limit block 26, a spring 27, a forefinger component base board 18, a vertical guide rail 20 and a connecting plate 17. The rubber covers 23 and 25 are fixed on the rollers 22 and 24 respectively by an interference fit. The rollers 22 and 24 are supported fixedly by the bearing unit 21. The bearing unit 21 is fixed on the forefinger component base board 18 by the horizontal guide rail 19. The limit block 26 is used to limit a limitation position of the bearing unit 21. The forefinger component base board 18 is connected to a screw rod output of the driving component 1 through the connecting plate 17 and to the fixed pedestal of the driving component 1 through the vertical guide rail 20.

The forefinger component pedestal 21 makes rubber covers 23, 25 of the forefinger component be tightly pressed on the corresponding rubber covers of the thumb component by the pull force of spring 27. The forefinger component 4 cooperates with the thumb component 3 to realize the rotation and advancement of the catheter/guide wire. The catheter/guide wire can make a rotation movement through the rotation of roller 9 and 10 of the thumb component. When the screw rod of the driving component 1 drives the connecting plate 17, the rubber covers 23, 25 of the forefinger component and the rollers 8, 11 of the thumb component 3 can move linearly along the opposite directions. Then the catheter/guide wire can make a clockwise or counterclockwise rotation.

Figure 4:
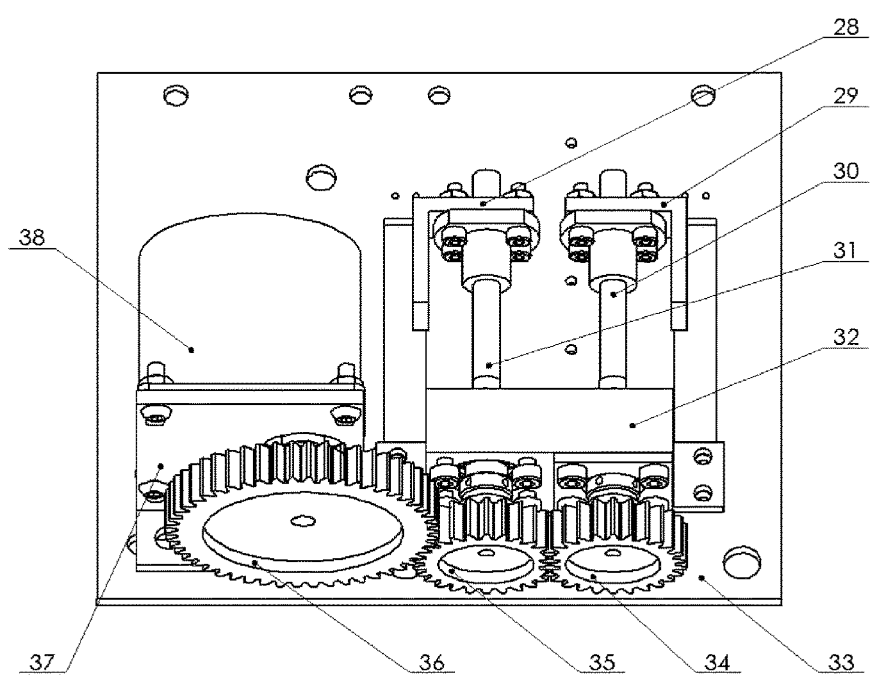
FIG. 4 shows a structure of the driving component of the catheter or guide wire manipulating device with two-point-clamping for vascular intervention according to the embodiment of the disclosure.

FIG. 4 shows a structure of the driving component 1. The driving component may include a rotating motor 38, a motor frame 37, a gear 36, a pinion 34, a pinion 35, a base board 33, a bearing unit 32, a screw rod 31, a screw rod 30, a nut connecting frame 25 and a nut connecting frame 24. The rotating motor 38 is connected to the motor frame 37 by bolts. The output shaft of motor 38 is fixedly connected to the gear 36. The pinion 35 is engaged with the gear 36, and the pinion 35 is engaged with the pinion 34. The pinion 35 is connected to the end of screw rod 30. The screw rods 31 and 30 are both supported by the bearing unit 32. The nut connection frames 24 and 25 are respectively connected to the nuts of screw rod 27 and 26. The screw pitch of the two screw rods 31 and 30 may be the same. The motor frame 37 and the bearing unit 32 are all fixed on the base board 33. The driving component 1 is used to drive the movement of the thumb component 3 and the forefinger component 4. The transmission is as follows. The output shaft of motor 38 drives the gear 36 to be rotated. Pinion 35 is engaged with the gear 36. Similarly, the pinion 35 is engaged with the pinion 33. Then the nuts of screw rods 31 and 30 allow linear movement along the opposite direction. The movement is transmitted to the thumb component 3 and the forefinger component 4 through the nut connecting frames 28 and 29.

Figure 5:
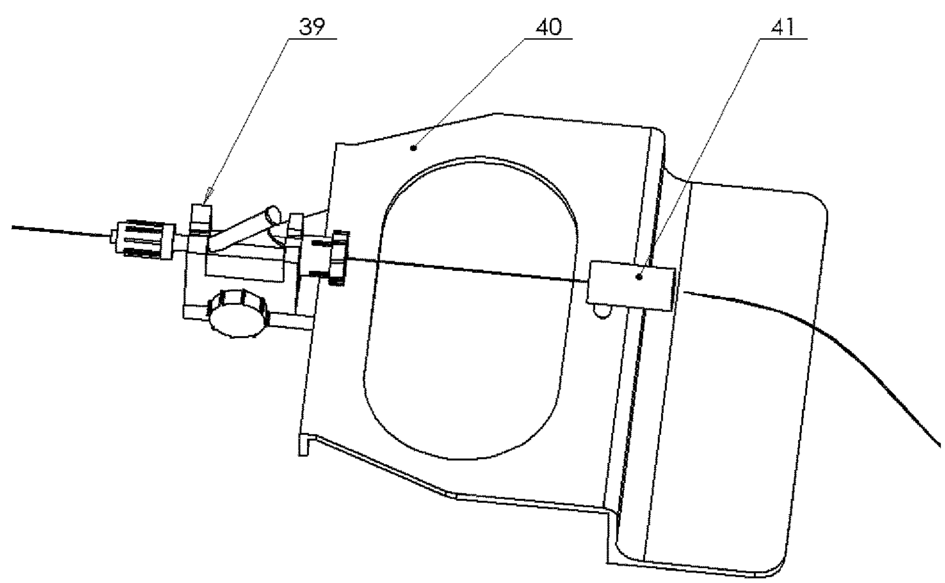
FIG. 5 shows a structure of the catheter/guide wire support component of the catheter or guide wire manipulating device with two-point-clamping for vascular intervention according to the embodiment of the disclosure.

FIG. 5 shows a structure of catheter/guide wire support component. The catheter/guide wire support component includes Y adapter fixation 39, an entry support 41 and a top plate 40. The Y adapter fixation 39 is configured to install a Y adapter quickly. The entry support is a hollow structure to support the catheter/guide wire when the catheter/guide wire is transmitted into the mechanism. When a Y adapter is loaded on the Y adapter fixation 39, both center lines of the Y adapter and the entry support 41 should be collinear.

The catheter or guide wire manipulating device drives the catheter/guide wire to move along two directions: advancement and rotation. The advancement driven by the advancing motor 16 of the catheter/guide wire is attached to the rotation driven by the rotating motor 38.

When clamping the catheter/guide wire, the rollers 22 and 24 of the forefinger component 4 can be moved manually away from the rollers 9 and 10 of the thumb component 3. After being released, the rollers 22 and 24 and the rollers 9 and 10 are tightly pressed by the pull force of spring 27.

The advancement transmission of the catheter/guide wire is as follows. The output shaft of the advancing motor 16 transmits the movement to the roller 9 through the engagement between the gear 14 and the gear 12. Then the movement is transmitted to the roller 10 through the engagement between the gear 14 and the gear 13 to drive rubber cover 8 and 11 to rotate, while, the catheter/guide wire is pressed by the rollers 22 and 24 of the forefinger component through the spring 27 so that the catheter/guide wire is driven to advance by the friction.

The rotation of rotating motor 38 is transmitted to the input of the two screw rods (31 and 30) through the gear transmission (gear 36, pinions 35, 34) with the same speed but along opposite directions. The movement is transmitted to the guide rail 6 and the vertical guide rail 20, which are respectively connected to the connecting plate 5 of the thumb component and the connecting plate 17 of the forefinger component. Then the rollers 9, 10 of the thumb component and rollers 22, 24 of forefinger component move vertically along the opposite directions. Simultaneously, the rubber covers 23, 8, 25, 11 are pressed by the pull force of spring 27 and the friction drives the catheter/guide wire to rotate.

The rotating motor 38 and the advancing motor 16 can be controlled simultaneously because the two motions are structural decoupling. Therefore the simultaneous rotation motion and advancement motion of the catheter/guide wire are allowed.

The above detailed embodiments describe the object, technical solutions and advantages of the disclosure in further detail. It shall be appreciated that the above contents are just detailed embodiments of the disclosure and are not intended to limit the disclosure. Any alternative, equivalent replacements, improvements, etc. made within the spirit and scope of the disclosure shall be encompassed by the scope of the disclosure.

What is claimed is:

1. A catheter or guide wire manipulating device with two-point-clamping for vascular intervention comprising a thumb component, a forefinger component, a driving component and a catheter/guide wire support component;

the thumb component comprises a set of rollers configured to advance or retreat the catheter/guide wire; the thumb component is configured to drive the catheter/guide wire to rotate clockwise or counterclockwise by a combination motion of the thumb component and the forefinger component;

the forefinger component is configured to cooperate with the thumb component to implement the rotation and advancement of the catheter/guide wire by moving the forefinger component manually away from the thumb component, and the forefinger component returning by a pull force of a spring after being released;

the driving component is configured to drive the thumb component and the forefinger component; the driving component include a rotating motor, gears, pinions and screw rods, the rotating motor drives gears to rotate, the gears are engaged with the pinion correspondingly, nuts of the screw rods make a linear movement along opposite directions so that the linear movement is supplied to the thumb component and the forefinger component, respectively;

the catheter/guide wire support component comprises a Y adapter fixation configured to install a Y adapter and an entry support configured to support and guide the catheter/guide wire into a mechanism; the entry support has a hollow structure to support the catheter/guide wire when the catheter/guide wire is transmitted into the mechanism;

wherein the thumb component includes a pair of rollers, a pair of rubber covers, a bearing unit, a gear, an advancing motor and a guide fixed plate; the advancing motor is fixed to the motor frame with bolts; a motor output shaft of the advancing motor is connected to the pair of two rollers through a gear transmission; the pair of rollers are supported fixedly by the bearing unit and the pair of rubber covers are made of rubber and mounted on the pair of rollers by an interference fit respectively.

2. The catheter or guide wire manipulating device according to claim 1, wherein the catheter or guide wire manipulating device is configured to manipulate the catheter/guide wire to implement advancement motion and rotation motion along two directions; the advancement motion of catheter/guide wire is attached to the rotation motion of the catheter/guide wire.

3. The catheter or guide wire manipulating device according to claim 1, wherein, the roller of the thumb component is configured to rotate to make the catheter/guide wire advance or retreat by making the drive shaft rotate through the gear transmission, driving the roller of the thumb component to rotate by a rotation of the advancing motor output shaft and driving the catheter/guide wire to advance or retreat with the spring's pull force at two points between the rubber cover of the thumb component and the rubber cover of the forefinger component.

4. The catheter or guide wire manipulating device according to claim 3, wherein the catheter/guide wire is configured to rotate clockwise or counterclockwise via a combined motion of the thumb component and forefinger component by connecting the rollers, the rubber covers, the bearing unit, the motor frame, the gears and the advancing motor of the thumb component as a whole part to the driving component through a connecting plate, moving the whole part linearly up and down with a guidance of guide rails, while driving the roller of forefinger component by the driving component to move linearly in an opposite direction to a motion direction of the whole part.

5. The catheter or guide wire manipulating device according to claim 4, wherein the forefinger component includes a pair of rollers, a pair of rubber covers, a bearing unit, a forefinger component pedestal, a spring, a horizontal guide rail, a forefinger component base board, a vertical guide rail and a connecting plate; the rubber covers are fixed to the rollers by an interference fit respectively; the rollers are supported fixedly by the bearing unit fixed on the forefinger component base board by the horizontal guide rail; the forefinger component base board is connected to a fixed pedestal of the driving component through the vertical guide rail and to a screw rod output of the driving component through the connecting plate; the forefinger component pedestal is configured to press tightly the rollers of the forefinger component and the rollers of the thumb component respectively by the bearing unit through a pull force of a spring.

6. The catheter or guide wire manipulating device according to claim 5, wherein the thumb component further includes a guide rail and a connecting plate, the catheter/guide wire is driven to rotate clockwise or counterclockwise through a combination motion of two fingers on the thumb component and the forefinger component can drive by connecting the rollers, the rubber covers, the bearing unit, the motor frame, the gears and the advancing motor as a whole part to the driving component through the connecting plate, moving the whole part linearly up and down with a guidance of the guide rail, while driving the rubber covers of rollers by the driving component to move linearly along opposite directions so that the catheter/guide wire is rotated when being pressed by the rubber covers.

* * * * *